US006995133B1

(12) United States Patent
Prieto Valtueña et al.

(10) Patent No.: US 6,995,133 B1
(45) Date of Patent: Feb. 7, 2006

(54) UTILIZATION OF INTERFERON ALPHA 5 IN THE TREATMENT OF VIRAL HEPATOPATHIES

(75) Inventors: Jesús Prieto Valtueña, Navarra (ES); Ma Pilar Civeira Murillo, Navarra (ES); Esther Larrea Leoz, Navarra (ES)

(73) Assignee: Proyecto de Biomedicina CIMA, S.L., Pamplona (ES)

( * ) Notice: Subject to any disclaimer, the term of this patent is extended or adjusted under 35 U.S.C. 154(b) by 0 days.

(21) Appl. No.: 09/674,445

(22) PCT Filed: May 13, 1999

(86) PCT No.: PCT/ES99/00134

§ 371 (c)(1),
(2), (4) Date: Nov. 1, 2000

(87) PCT Pub. No.: WO99/58143

PCT Pub. Date: Nov. 18, 1999

(30) Foreign Application Priority Data

May 13, 1998 (ES) .................................... 9801003

(51) Int. Cl.
*A61K 38/00* (2006.01)
*A61K 38/21* (2006.01)
(52) U.S. Cl. ........................ 514/2; 514/12; 514/893; 514/894; 424/85.4; 424/85.7
(58) Field of Classification Search ............... 424/85.4, 424/85.7; 514/2, 12, 893, 894; 435/69.1, 435/69.51, 70.1, 71.2
See application file for complete search history.

(56) References Cited

U.S. PATENT DOCUMENTS 5,914,111 A * 6/1999 Wallner et al. ........... 424/134.1
6,007,805 A * 12/1999 Foster et al. .............. 424/85.7
6,172,046 B1 * 1/2001 Albrecht ....................... 514/43

OTHER PUBLICATIONS

Salmanian, A-H. et al., Synthesis and Expression of the gene for huamn epidermal growth factor in transgenic potato plants. (1996), Biotechnology Letters, vol. 18 No. 9, pp 1095-1098.*
Davis, G.L. et al. "Treatment of Chronic Hepatitis C With Recombinant Interferon Alfa: A Multicenter Randomized, Controlled Trial" *New England Journal of Medicine* vol. 321, No. 22 (1989) pp 1501-1506.
Di Bisceglie, A.M. et al. "Recombinant Interferon Alfa Therapy for Chronic Hepatitis C: A Randomized, Double-Blind, . . . trial" *New England Journal of Medicine* vol. 321, No. 22 (1989) pp 1506-1510.
Soriano, V. et al. "Efficacy and Safety of α-Interferon Treatment for Chronic Hepatitis C in HIV-infected Patients" *Journal of Infection* vol. 31, (1995) pp. 9-13.

Mauss, S. et al. "Response to Treatment of Chronic Hepatitis C with Interferon α in Patients Infected with HIV-1 Is Associated with Higher CD4+ Cell Count" *Infection* vol. 26, No. 1 (1998) pp. 16-19.
Soriano, V. et al. "Interferon α for the Treatment of Chronic Hepatitis c in Patients Infected with Human Immunodeficiency Virus" *Clinical Infectious Diseases* vol. 23 (1996) pp. 585-591.
Aguet, M. et al. "Various Human Interferon α Subclasses Cross-React with Common Receptors: Their Binding Affinities Correlate with Their Specific . . . Activities" *Virology*, vol. 132, p. 211-216, (1984).
Au, W.C. et al. "Virus-Mediated Induction of Interferon A Gene Requires Cooperation Between Multiple Binding Factors . . . Region" *Journal of Biological Chemistry*, vol. 268, No. 32, p. 24032-24040, (1993).
Bisat, F. et al. "Differential and Cell Type Specific Expression of Murine Alpha-Interferon Genes is Regulated on the Transcriptional Level" *Nucleic Acids Research*, vol. 16, No. 13, p. 6067-6083, (1988).
Brandt, E.R. et al. "Expression of IFN A Genes in Subpopulations of Peripheral Blood Cells" *British Journal of Haematology*, vol. 86, p. 717-725, (1994).
Chomczynski, P. et al. "Single-Step Method of RNA Isolation by Acid Guanidinium Thiocyanate-Phenol-Chloroform Extraction" *Analytical Biochemistry*, vol. 162, p. 156-159, (1987).
Derynck, R. et al. "Isolation and Structure of a Human Fibroblast Interferon Gene" *Nature*, vol. 285, p. 542-547, (1997).

(Continued)

*Primary Examiner*—Janet Andres
*Assistant Examiner*—Jegatheesan Seharaseyon
(74) *Attorney, Agent, or Firm*—Ladas & Parry LLP

(57) ABSTRACT

The invention relates to the use of interferon alpha 5 in the treatment of viral hepatopathies. The invention describes the reduced synthesis of IFNα5 in the livers of patients with hepatitis C in comparison to healthy livers. The sub-type of IFN expressed in said healthy livers corresponded only to the subtype alpha 5 in comparison with the different sub-types expressed in ill livers. The sequence SEQ ID NO:1 shows the partial sequence of cDNA corresponding to IFNα5. These significant differences between the expression patterns of some livers an others demonstrate the importance of the use of such interferon sub-type in the fabrication of compositions useful in the treatment of viral hepatopathies. The invention discloses in details such utilization in different forms and processes, including those which use the production of recombinant proteins from sequences of the type SEQ ID NO:1.

9 Claims, 3 Drawing Sheets

OTHER PUBLICATIONS

Fattovich, G. et al. "Morbidity and Mortality in Compensated Cirrhosis Type C: A Retrospective Follow-up . . . Patients" Gastroenterology, vol. 112, p. 463-472, (1997).

Foster, G.R. et al. "Differential Relative Activities of Human Cell-Derived Interferon-α Subtypes: IFN-α8 Has Very . . . Potency" Journal of Interferon and Cytokine Research, vol. 16, p. 1027-1033, (1996).

Geldelman, H.E. et al. "A Selective Defect of Interferon α Production in Human Immunodeficiency Virus-Infected Monocytes" Journal of Experimental Medicine, vol. 172, p. 1433-1442, (1990).

Gil, B. et al. "Hepatic and Extrahepatic HCV RNA Strands in Chronic Hepatitis C: Different Patterns of Response to Interferon Treatment" Hepatology, vol. 18, p. 1050-1054, (1993).

Goeddel, D.V. et al. "The Structure of Eight Distinct Cloned Human Leukocyte Interferon cDNAs" Nature, vol. 290, p. 20-26, (1981).

Hiscott, J. et al. "Differential Expression of Human Interferon Genes" Nucleic Acids Research, vol. 12, No. 9, (1984).

Knodell, R.G. et al. "Formulation and Application of a Numerical Scoring System for Assessing Histological Activity in Asymptomatic . . . Hepatitis" Hepatology, vol. 1, No. 5, p. 431-435, (1981).

Larrea, E. et al. "Tumor Necrosis Factor α Gene Expression and the Response to Interferon in Chronic Hepatitis C" Hepatology, vol. 23, p. 210-217, (1996).

Lopez, S. et al. "Silencer Activity in the Interferon-A Gene Promoters" Journal of Biological Chemistry, vol. 272, No. 36, p. 22788-22799, (1997).

De Maeyer, E. et al. "Interferons" The Cytokine Handbook, Chapter 11, p. 215-239, (1991).

Ng, S.Y. et al. "Evolution of the Functional Human β-Actin Gene and Its Multi-Pseudogene Family: Conservation . . . Pseudogenes" Molecular and Cellular Biology, vol. 5, No. 10, p. 2720-2732, (1985).

Poynard, T. et al. "Natural History of Liver Fibrosis Progression in Patients with Chronic Hepatitis C" The Lancet, vol. 349, p. 825-832, (1997).

Samuel, C.E. "Antiviral Actions of Interferon Interferon-Regulated Cellular Proteins and Their Surprisingly Selective Antiviral Activities" Virology, vol. 183, p. 1-11, (1991).

Sarobe, P. et al. "Production of Interleukin-2 in Response to Synthetic Peptides from Hepatitis C Virus E1 Protein in Patients . . . Treatment" Journal of Hepatology, vol. 25, p. 1-9, (1996).

Tilg, H. "New Insights Into the Mechanisms of Interferon Alfa: An Immunoregulatory and Anti-inflammatory Cytokine" Gastroenterology, V. 112, p. 1017-1021, (1997).

Tovey, M.G. et al. "Interferon Messenger RNA is Produced Constitutively in the Organs of Normal Individuals" Proc. Natl. Acad. Sci., vol. 84, p. 5038-5042, (1987).

Viazov, S. et al. "Typing of Hepatitis C Virus Isolates by DNA Enzyme Immunoassay" Journal of Virological Methods, vol. 48, p. 81-92, (1994).

Weissmann, C. et al. "The Interferon Genes" Progress in Nucleic Acid Research and Molecular Biology, vol. 33, p. 251-300, (1986).

* cited by examiner

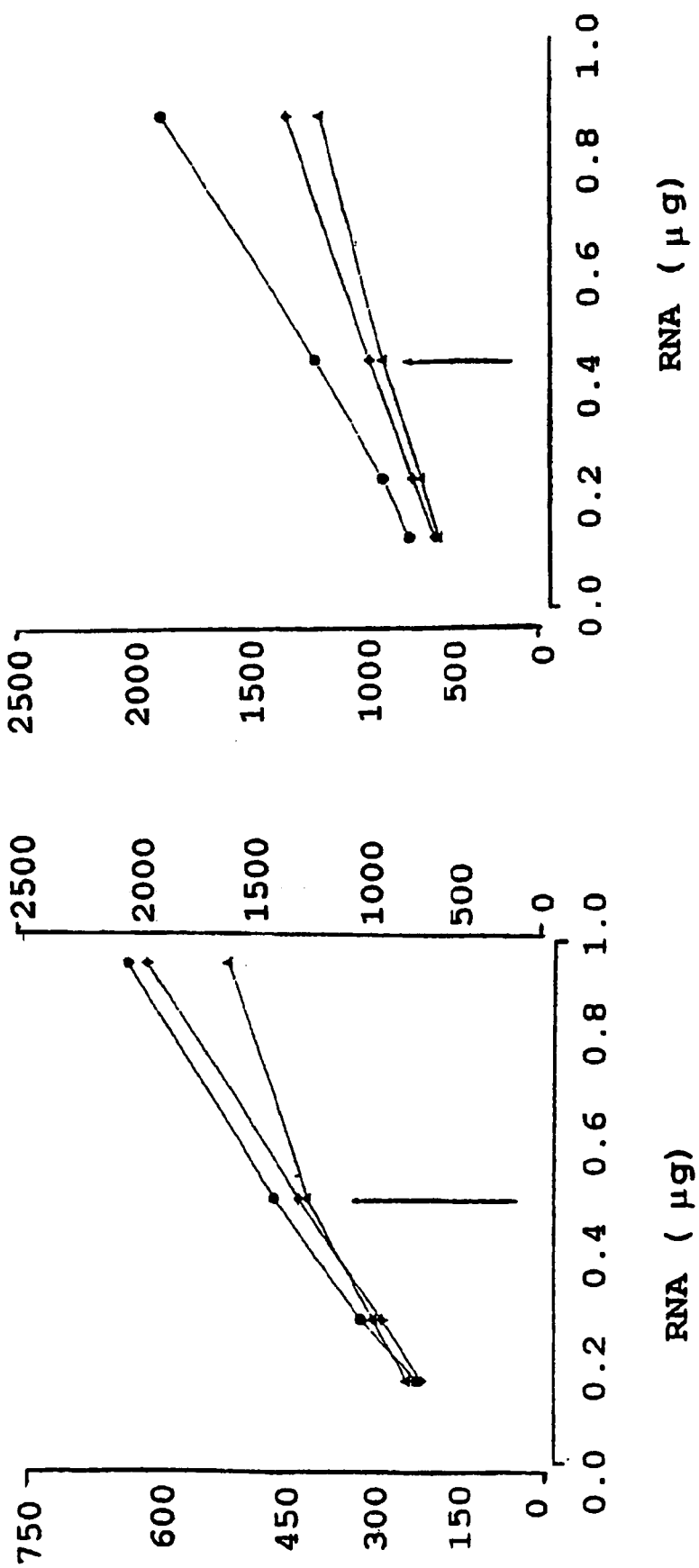

SEQUENCE LISTING

<160> NUMBER OF SEQ ID NOS: 8

<210> SEQ ID NO 1
<211> LENGTH: 274
<212> TYPE: DNA
<213> ORGANISM: Homo sapien
<220> FEATURE:
<223> OTHER INFORMATION: Nucleotides 672 - 945 in the sequence of the
    IFNa5 gene published in the Genbank database under access number
    X02956.

<400> SEQUENCE: 1

```
tc cat gag atg atc cag cag acc ttc aat ctc ttc agc aca aag gac tca     50
   His Glu Met Ile Gln Gln Thr Phe Asn Leu Phe Ser Thr Lys Asp Ser
    1               5                  10                  15 tct gct act tgg gat gag aca ctt cta gac aaa ttc tac act gaa ctt tac    101
Ser Ala Thr Trp Asp Glu Thr Leu Leu Asp Lys Phe Tyr Thr Glu Leu Tyr
             20                  25                  30 cag cag ctg aat gac ctg gaa gcc tgt atg atg cag gag gtt gga gtg gaa    152
Gln Gln Leu Asn Asp Leu Glu Ala Cys Met Met Gln Glu Val Gly Val Glu
         35                  40                  45                  50 gac act cct ctg atg aat gtg gac tct atc ctg act gtg aga aaa tac ttt    203
Asp Thr Pro Leu Met Asn Val Asp Ser Ile Leu Thr Val Arg Lys Tyr Phe
                     55                  60                  65 caa aga atc acc ctc tat ctg aca gag aag aaa tac agc cct tgt gca tgg    254
Gln Arg Ile Thr Leu Tyr Leu Thr Glu Lys Lys Tyr Ser Pro Cys Ala Trp
             70                  75                  80 gag gtt gtc aga gca gaa at                                             274
Glu Val Val Arg Ala Glu
85                  90
```

<210> SEQ ID NO 2
<211> LENGTH: 20
<212> TYPE: DNA
<213> ORGANISM: Artificial Sequence
<220> FEATURE:
<223> OTHER INFORMATION: Primer to amplify a fragment of 274 base pairs
    located between nucleotides 240 - 514 in the human IFNa gene

<400> SEQUENCE: 2
tccatgagat gatccagcag                                                   20

<210> SEQ ID NO 3
<211> LENGTH: 22
<212> TYPE: DNA
<213> ORGANISM: Artificial Sequence
<220> FEATURE:
<223> OTHER INFORMATION: Primer to amplify a fragment of 274 base pairs
    located between nucleotides 240 - 514 in the human IFNa gene

<400> SEQUENCE: 3
atttctgctc tgacaacctc cc                                                22

<210> SEQ ID NO 4
<211> LENGTH: 21
<212> TYPE: DNA
<213> ORGANISM: Artificial Sequence
<220> FEATURE:
<223> OTHER INFORMATION: Primer to amplify a fragment of 276 base pairs
    located between nucleotides 349 - 625 of cDNA of human IFN gene

<400> SEQUENCE: 4
tctagcactg gctggaatga g                                                 21

```
<210> SEQ ID NO 5
<211> LENGTH: 21
<212> TYPE: DNA
<213> ORGANISM: Artificial Sequence
<220> FEATURE:
<223> OTHER INFORMATION: Primer to amplify a fragment of 276 base pairs
      located between nucleotides 349 - 625 of cDNA of human IFN gene

<400> SEQUENCE: 5
gtttcggagg taacctgtaa g                                              21

<210> SEQ ID NO 6
<211> LENGTH: 20
<212> TYPE: DNA
<213> ORGANISM: Artificial Sequence
<220> FEATURE:
<223> OTHER INFORMATION: Primer to amplify a fragment of 314 base pairs
      (nucleotides 1319 - 2079) of the -actin gene

<400> SEQUENCE: 6
tctacaatga gctgcgtgtg                                                20

<210> SEQ ID NO 7
<211> LENGTH: 20
<212> TYPE: DNA
<213> ORGANISM: Artificial Sequence
<220> FEATURE:
<223> OTHER INFORMATION: Primer to amplify a fragment of 314 base pairs
      (nucleotides 1319 - 2079) of the -actin gene

<400> SEQUENCE: 7
ggtgaggatc ttcatgaggt                                                20

<210> SEQ ID NO 8
<211> LENGTH: 23
<212> TYPE: DNA
<213> ORGANISM: Artificial Sequence
<220> FEATURE:
<223> OTHER INFORMATION: DNA fragment for use in determining C virus
      genotype

<400> SEQUENCE: 8
grccgtcttg gggccmaaat gat                                            23
```

UTILIZATION OF INTERFERON ALPHA 5 IN THE TREATMENT OF VIRAL HEPATOPATHIES

FIELD OF INVENTION

The invention relates to the production of interferon alpha 5 for use in compositions useful in the treatment of liver diseases of viral origin.

We have shown that IFN-alpha 5 is the sole subtype of alpha interferon produced in the healthy liver and that its levels are clearly reduced in chronic hepatitis C, which suggests that this substance may be of therapeutic value in the treatment of this disease and other forms of viral hepatitis. Knowing the coding gene sequence for this interferon, its production through recombinant DNA technology in different hosts makes it possible to develop effective drugs for the treatment of liver diseases of this type at their different stages of development.

BACKGROUND OF INVENTION

Infected cells can recognize the presence of a virus by sending out signals which result in the transcription and secretion of type I interferon (IFNα and IFNβ). IFNα is a family of thirteen polypeptides (subtypes) coded by different genes. IFNβ is a glycoprotein produced by a single gene. Different cell types produce both IFNα and IFNβ (1, 2).

Viral infection is the main stimulus for the production of type I interferon, although there are other factors which can increase its synthesis, such as bacterial components, double chain RNA, growth factors and other cytokines (1). In addition to having its antiviral effect, IFNα can interact with certain cytokines and with T cells regulating the growth and differentiation of the cells in the immune system (3). IFNα genes are expressed as a matter of course in human tissue in healthy individuals (4), while the expression of particular subtypes is restricted to certain cell types (5, 6). The induction of IFN by viruses is mainly regulated at transcription level. The specific activation of transcription occurs through the interaction of cell factors induced by viruses with the domains regulating the promoters of IFNα genes (7).

All IFNα and IFNβ subtypes have a common receptor at the cell surface. Competitive binding tests at the receptor for different IFNα subtypes indicate that all of these combine at the same receptor, but with different affinities (8). The biological activity of the different subtypes of IFNα is little known. The IFNα 5 and IFNβ 8 interferon subtypes appear to be those having the greatest antiviral activity. Antiproliferative response also differs between the different subtypes (9). In humans unstimulated peripheral blood mononuclear cells express different IFNα subtypes (10).

A common mechanism for the persistence of viral infection is avoidance of the IFN system. Many viruses have developed strategies to avoid the antiviral effects of IFN. Specifically, a selective defect in the production of IFNα has been described in monocytes infected by human immunodeficiency virus (11).

Hepatitis C virus (HCV) is a single chain RNA virus which results in chronic infection in more than two thirds of persons infected. The prevalence of infection by HCV is around 2 to 3% in the population of the West. Studies performed in Europe show that 33% of patients with chronic HCV infection develop cirrhosis in a mean period of less than 20 years (12). A significant proportion of these patients develop liver cancer, with an annual incidence of 1.4% (13).

It has been difficult to find the reason for the high level of persistence of HCV infection. The high rate of mutations in the virus and the production of a predominant profile of Th2 cytokines in comparison with Th1 have been described as being responsible for this high level of persistence by the infection. Treatment with IFN induces a sustained response in around 30% of patients with chronic hepatitis C. The mechanism responsible for response or non-response to treatment with IFN is little understood.

The IFN system has only been studied in chronic HCV infection. There is no appropriate animal model for chronic HCV infection, and, because of this, investigations performed on humans are the only source of information on the pathophysiology and pathogenesis of chronic hepatitis C. This invention describes the expression of IFNα and IFNβ genes in the liver and in the peripheral blood mononuclear cells (PBMC) in healthy controls and patients with chronic hepatitis C. In addition to this we have analysed the IFNα subtype expressed in normal liver tissue and the liver tissue of patients with chronic hepatitis C. Expression of the different IFNα subtypes has also been analysed in PBMC in healthy controls and patients with chronic hepatitis C.

REFERENCES

1. Maeyer E, Maeyer-Guignard J. Interferons. In Thomson A, ed. The Cytokine Handbook. London: Academic Press Limited 1991: 215–239.
2. Samuel C E. Antiviral Actions of Interferon. Interferon-Regulated Cellular Proteins and Their Surprisingly Selective Antiviral Activities. Virology 1991; 183: 1–11.
3. Tilg H. New Insights Into the Mechanisms of Interferon Alfa: An Immunoregulatory and Anti-inflammatory Cytokine. Gastroenterology 1997; 112: 1017–1021.
4. Tovey M G, Streuli M, Gresser I, Gugenheim I, Blanchard B, Guymarho J, Vignaux F and Gigou M. Interferon messenger RNA is produced constitutively in the organs of normal individuals. Proc. Natl. Acad. Sci. USA 1987; 84: 5038–5042.
5. Bisat F, Raj N B, Pitha P M. Differential and cell type specific expression of murine alpha interferon genes is regulated on the transcriptional level. Nucleic Acids Res 1988; 16:6067–6083.
6. Hiscott J, Cantell K, Weissmann C. Differential expression of human interferon genes. Nucleic Acids Res 1984; 12:3727–3746.
7. Au W C, Su Y, Raj N B K and Pitha P M. Virus-mediated Induction of Interferon A Gene Requires Cooperation between Multiple Binding Factors in the Interferon α Promoter Region. The Journal of Biological Chemistry 1993, 268: 24032–24040.
8. Aguet M, Grobke M, Dreiding P. Various human interferon alpha subclasses cross-react with common receptors: their binding affinities correlate with their specific biological activities. Virology 1984; 132:211–216.
9. Foster G R, Rodrigues 0, Ghouze F, Schulte-Frohlinde D, Testa D, Liao M J, Stark G R, Leadbeater L, Thomas H C. Different relative activities of human cell derived interferon-alpha subtypes: interferon alpha 8 has very high antiviral potency. J Interferon and Cytokine Res. 1996; 16:1027–1033.
10. Brandt E R, Linnane A W, Devenish R J. Expression of IFN A genes in subpopulations of peripheral blood cells. Br J Haematol 1994; 86:717–725.

11. Gendelman H E, Friedman R M, Joe S, Baca L M, Turpin J A, Dveksker G, Meltzer M S and Dieffenbach C. A Selective Defect of Interferon α Production in Human Immuno-deficiency Virus-infected Monocytes. The Journal of Experimental Medicine 1990; 172: 1433–1442.
12. Poynard T, Bedossa P, Opolon P. Natural history of liver fibrosis progression in patients with chronic hepatitis C. The OBSVIRC, METAVIR, CLINIVIR, and DOSVIRC groups. Lancet 1997; 349:825–832.
13. Fattovich G, Giustina G, Degos F et al. Morbidity and Mortality in Compensated Cirrhosis Type C: A Retrospective Follow-Up Study of 384 Patients. Gastroenterology 1997; 112: 463–472.
14. Gil B, Qian Ch, Riezu-Boj J I, Civeira M P, Prieto J. Hepatic and extrahepatic HCV RNA strands in chronic hepatitis C: different patterns of response to interferon treatment. Hepatology 1993; 18:1050–1054.
15. Lopez S, Reeves R, Island M L, Bandu M T, Christeff N, Doly J and Navarro S. Silencer Activity in the Interferon-A Gene Promoters. The Journal of Biological Chemistry 1997; 272: 22788–22799.
16. Knodell R, Ishak K, Black W, Chen T, Craig R, Kaplowitz N, Kiernan T, et al. Formulation and application of a numerical scoring system for assessing histological activity in asymptomatic chronic active hepatitis. Hepatology 1981; 1:431–435.
17. Chomczynsky P; Sacchi N. Single-step of RNA isolation by acid guanidinium thiocyanate-phenol-chloroform extraction. Anal. Biochem. 1987; 162:156–159.
18. Weissmann C, Weber H. The interferon genes. Prog Nucleic Acid Res Mol Biol 1986; 33:251–300.
19. Goeddel D V, Leung D W, Dull T J, Gross M, Lawn R M., McCandliss R, Seeburg P H, Ullrich A, Yelverton E, Gray P W. The structure of eight distinct cloned human leukocyte interferon cDNAs. Nature 1981; 290:20–26.
20. Derynck R, Content J, DeClercq E, Volckaert G, Tavernier J, Devos R, Fiers W. Isolation and structure of a human fibroblast interferon gene. Nature 1980; 285:542–547.
21. Ng S Y, Gunning P, Eddy R, Ponte P, Leavitt J, Shows T, Kedes L. Evolution of the functional human b-actin gene and its multi-pseudogene family: conservation of noncoding regions and chromosomal dispersion of pseudogenes. Mol Cell Biol 1985; 5:2720–2732.
22. Larrea E, Garcia N, Qian Ch, et al. Tumor Necrosis Factor α Gene Expression And The Response To Interferon In Chronic Hepatitis C. Hepatology 1996; 23: 210–217.
23. Viazov S, Zibert A, Ramakrishnan K; Widell A; Cavicchini A, Schreier E; Roggendord M. Typing of hepatitis C virus isolates by DNA enzyme immunoassay. J. Virol. Methods 1994; 48:81–92.
24. Sarobe P, Jauregui J I, Lasarte J J, García N, Civeira M P, Borrás-Cuesta F and Prieto J. Production of interleukin-2 in response to synthetic peptides from hepatitis C virus E1 protein in patients with chronic hepatitis C: relationship with the response to interferon treatment. J Hepatol 1996; 25:1–9.

BRIEF DESCRIPTION OF THE DRAWINGS

FIGS. 3 A–B: Relationship between the initial quantity of total RNA (abscissa) and the strength of the PCR product band obtained by amplifying the RNAm of IFNα (•), IFNβ (▲) and β-actin (♦) (ordinate, as counts×mm$^2$) in PBMC (A) and liver (B) samples.

DETAILED DESCRIPTION

Patients and Controls

Figures 1A, 1B:
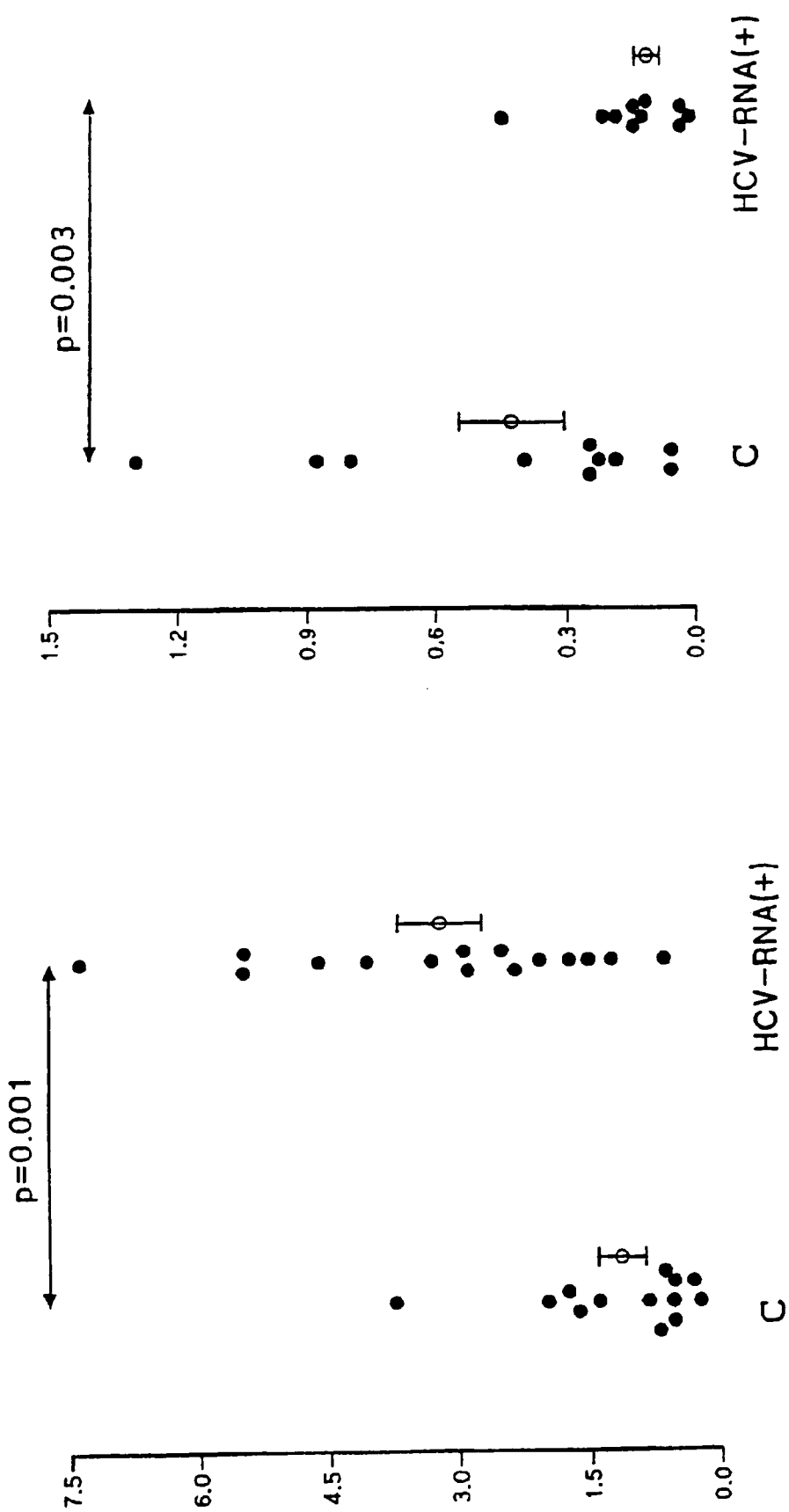
FIGS. 1 A–B: Expression of alpha interferon/β-actin RNAm (ordinate) in peripheral blood mononuclear cells (A) and in the liver (B) of healthy controls and patients with chronic hepatitis C (HCV-RNA+) (abscissa).

The expression of IFNα and IFNβ genes was analysed in samples from liver biopsies from 16 patients with chronic hepatitis C (9 men and 7 women, age range 24 to 71 years). Five of these patients showed cirrhosis. The viral genotype was determined in 14 patients and was 1b in 10 patients, 1a in 2 patients and genotype 3 in 1 patient.

In addition to this, expression of the IFNα and IFNβ genes was determined in 12 samples of normal liver obtained by laparotomy from 12 control patients (9 men and 3 women, age range 49 to 70 years). The laparotomies were performed on account of the presence of digestive tumours in 10 patients (4 colo-rectal, 5 gastric and 1 pancreatic) due to chronic pancreatitis in 1 patient and the presence of a hydatid cyst in another patient. Liver histology was normal in the twelve cases. None of these control cases had received treatment before the liver sample was obtained.

mRNA levels of IFNα and IFNβ were also determined in PBMC in 25 patients with chronic hepatitis C (14 men and 11 women, age range 24 to 69 years) (four of these patients had cirrhosis) and in PBMC from 23 healthy controls (10 men and 13 women, age range from 25 to 66 years). The viral genotype for these patients was 1b in 22 patients, 1a in two patients and 3 in 1 patient.

The diagnosis of chronic hepatitis C was based on an increase in serum transaminases lasting more than 6 months, a positive result for anti-HCV antibodies (2nd generation ELISA, Ortho Diagnostic System, Raritan, N.J., USA), the presence of C virus RNA in serum (reverse-reaction transcription in the polymerase chain), and histological evidence of chronic hepatitis. The severity of liver damage was evaluated using the Knodell index (16). Other causes of chronic hepatitis other than hepatitis C virus were ruled out. None of the patients had received treatment with IFNα during at least 6 months prior to the study.

Preparation of Liver, PBMC and Serum Samples

The liver samples were obtained by liver biopsy using a Tru-Cut biopsy needle (Baxter, Deerfield, Ill.). One third of the sample was immediately frozen in liquid nitrogen and kept at −80° C. until total RNA extraction took place. The remainder of the sample was used for the histological investigation.

PBMC were isolated from heparinized blood using a density gradient with Lymphoprep (Nycomed Pharma As, Oslo, Norway), centrifuged at 600 g for 30 minutes. After centrifuging the PBMC were collected, washed 5 times with 0.9% NaCl and lysed using Ultraspec™ protein denaturing solution (Biotech Laboratories, Houston, USA). The cellular lysate was kept at −80° C. until total RNA extraction was performed using the method of Chomcznski and Sacchi (17).

The serum samples were obtained by centrifuging from venous blood collected in sterile tubes. The serum was kept at −40° C. until use.

Analysis of the Expression of IFNα and IFNβ Genes in the Liver and PBMC mRNA levels of IFNα and IFNβ were determined using a quantitative polymerase chain reaction reverse transcription (RT-PCR) method using a thermocycler (Perkin-Elmer Gene Amp PCR system 2400). Prior to reverse transcription 2 μg of total RNA (from both the liver and PBMC) were treated with 1 unit of deoxyribonuclease (DNAse I amplification grade, Gibco-BRL, Gaithersburg, Md., USA) to eliminate possible contaminating DNA. The presence of traces of DNA was checked by including control reactions without reverse transcription. This step is required because of the absence of introns in IFNα and IFNβ genes (18), which made it impossible for us to distinguish the product of PCR from the RNA or possible contaminating DNA. All the controls performed without reverse transcription were negative, indicating the absence of contaminating DNA. Total RNA was transcribed (60 minutes at 37° C.) with 400 units of M-MuLV reverse transcriptase (Gibco-BRL, Gaithersburg, Md., USA) in a final volume of 40 μl of 5× saline solution (250 mM Tris-HCl pH 8.3, 375 mM KCl, 15 mM $MgCl_2$), supplemented with 5 mM DTT, 0.5 mM triphosphate dioxyribonucleotides (Boehringer Mannheim, Mannheim, Germany), 48 units of RNAsas inhibitor (Promega Corporation, Md., US) and 400 ng of random hexamers (Boehringer Mannheim, Mannheim, Germany). After denaturing the reverse transcriptase (95° C., 1 minute) and rapidly cooling over ice, a 10 μl aliquot (0.5 μg) of the cDNA was used to amplify the IFNα and IFNβ by PCR in 50 μl of 10×PCR buffer (160 mM $(NH_4)SO_4$, 670 mM Tris-HCl pH 8.8, 0.1% Tween 20) supplemented with the direction and antidirection primers (40 ng of each one for IFNα and 60 ng for IFNβ), 1.2 mM $MgCl_2$ and 2 units of Biotaq™ DNA polymerase (Bioline, London, LTK). Control reactions without RNA were performed in all the experiments. As an internal control for each sample a fragment of β-actin cDNA was amplified using a 10 μl aliquot of the cDNA obtained previously. The IFNα was amplified by performing 30 or 33 cycles (PBMC or liver respectively) (94° C., 60° C. and 72° C. during 20, 15 and 30 seconds for each step respectively), the INFβ was amplified by performing 30 or 35 cycles (PBMC or liver respectively) (94° C., 58° C. and 72° C. for 20, 15 and 30 seconds for each step respectively) and β-actin was amplified by reacting 18 or 25 cycles (PBMC or liver respectively) (94° C., 55° C. and 72° C. for 20, 15 and 30 seconds for each step respectively), protocols which avoid interference with the PCR reaction saturation stage. The oligonucleotides (5'-3') d(TCCATGAGATGATCCAGCAG) (SEQ ID NO:2) and d(ATTTCTGCTCTGACAACCTCCC) (SEQ ID NO:3) were used as direction and antidirection primers respectively to amplify a fragment of 274 pairs of bases located between nucleotides 240–514 in the human IFNα gene (19). These oligonucleotides are direction primers designed to amplify all the subtypes of IFNα. The oligonucleotides D(TCTAGCACTGGCTGGAATGAG) (SEQ ID NO:4) and d(GTTTCGGAGGTAACCTGTAAG) (SEQ ID NO:5) were the primers used to amplify a fragment of 276 base pairs located between nucleotides 349–625 of cDNA of human IFNβ (20) d(TCTACAATGAGCTGCGT-GTG) (SEQ ID NO:6) and d(GGTGAGGATCTTCAT-GAGGT) (SEQ ID NO:7) were the primers used to amplify a fragment of 314 base pairs (nucleotides 1319–2079) of the β-actin gene (21).

After the amplification reactions 20 μl of the PCR product were run in a 2% agarose gel containing ethidium bromide. The bands obtained were displayed using an ultraviolet lamp and were analysed using a commercial programme (Molecular Analyst/PC, Bio-Rad) capable of digitizing and analysing the image obtained. Finally the values corresponding to the expression of the IFNα and IFNβ genes were standardized with their β-actin correlates. The results are expressed as the quotient between the value of IFNα and IFNβ and the β-actin correlate. Previously we demonstrated that the mRNA of β-actin was expressed constantly both in the liver and in the PBMC of patients with chronic hepatitis C (22), which has enabled us to standardize IFNα and IFNβ values with those obtained for β-actin.

Validation curves for the PCR technique were prepared using known quantities of total RNA (from 0 up to 1 μg). As will be seen in FIG. 3, with the total initial RNA quantities used for IFNα, IFNβ and β-actin (0.5 μg, for both the liver and PBMC), we were within the linear range of the PCR amplification curve. The inter-test coefficient of variance for IFNα/β-actin was 22% and for IFNβ/β-actin it was 24%. The identity of the PCR product obtained was checked for IFNα and IFNβ by automatic sequencing (ABI prism™ 310 genetic analyser, Perkin Elmer).

Identification of IFNα Subtypes

Total RNA extraction, reverse transcription and the PCR reaction were performed as described above, using the IFNα direction primers mentioned. The PCR product obtained was cloned using the commercial TOPO TA cloning kit (Invitrogen, Leek, Holland). At least 6 clones from each insert were sequenced in an automatic ABI PRISM 310 sequencer (Perkin Elmer, Foster, Calif.), using the Dye Rhodamine Terminator Cycle Sequencing Kit (Perkin Elmer, Foster, Calif.).

Detection, Quantification and Genotyping of C Virus RNA

The presence of C virus RNA in serum was determined using the RT-PCR technique (14, 22), using 2 pairs of specific primers for the non-coding 5' region of the C virus genome. The C virus RNA was quantified using the competitive PCR technique previously described by ourselves (22). The viral genotype was determined using Viazov's method (23) as already described previously (22, 24). The test 5'G(R)CCGTCTTGGGGCC(M)AAATGAT (SEQ ID NO:8) was used to determine genotype 4.

Statistical Analysis

The IFNα and IFNβ results are presented as mean±standard error. The normality of the variables was studied using the Shapiro-Wilks test. Statistical analysis of IFNα and IFNβ values in PBMC or liver was performed using non-parametric tests (Mann-Whitney U test) or parametric tests (Student's T). The association between quantitative variables was investigated using the Pearson or Spearman correlation coefficient, as appropriate. Windows SPSS 6.0 program was used for the statistical analysis.

Production of Recombinant Protein

Expression and Purification of Human Interferon-α5 in *Escherichia coli:*

Despite the fact that the expression of cDNAs originating from eucaryote organisms in *Escherichia coli* in general ensures a high level of production, isolation and purification of the protein of interest involves complex procedures and low yields. For this reason expression vectors are used to help obtain merged proteins whose purification is reduced to an affinity chromatography step, with high yield and efficiency.

Construction of the Expression Vector and Acquisition of Recombinant Bacteria

The cDNA which codes for interferon-α5 is cloned in pET14b vector (available commercially from Novagen).

This vector provides a sequence which codes for a series of histidine residues (1 kDa) which are translated in phase with the cloned cDNA to yield a merged protein which includes a 1 kDa histidine tail at its terminal amine end and then interferon-α5, with a site between the two which can be cut by thrombin.

Once the expression vector has been obtained, competent bacteria of the BL21 (DE3) strain are prepared, as this strain contains a gene which can be induced by T7 RNA polymerase, which is a necessary requirement for the subsequent production of protein. The competent bacteria are converted with the vector previously obtained (pET14b with the cloned interferon-α5 cDNA). The transformed bacteria are selected by their growth in LB medium with ampicillin, as the vector contains a gene which is resistant to this antibiotic.

Expression and Purification of Interferon-α5:

The transformed bacteria are grown in LB medium with ampicillin at 37° C. until an optical density of 0.4 at 600 nm is obtained. Then expression of the recombinant protein with IPTG is induced at a final concentration of 0.5 mM. In this way the lac promoter is induced and as a consequence the T7 RNA polymerase prometer which contains the vector and which regulates the expression of the cloned cDNA is induced. The culture is grown for a further 4 hours under the same conditions.

To obtain the extracts, once the bacteria have grown, centrifuging is carried out at 4° C. The precipitated bacteria are resuspended in 10 mM Tris/HCl buffer, 10% saccharose, 2 mM 2-mercaptoethanol and protease inhibitors. Homogenization was performed ultrasonically by incubation for 30 minutes with lysozyme at 4° C. This breaks down the bacterial wall and improves the yield of the extraction process. The cytosol extract is obtained by centrifuging the homogenate at 100,000 g for 90 minutes. Protein production is checked by analysing the cytosol fraction by SDS-PAGE.

His-interferon-α5 merged protein is purified by chromatography of the cytosol extract in a 2 ml nickel column. The protein is eluted by washing the column with 1 M imidazole. The pure protein is processed with thrombin and the interferon-α5 is subsequently repurified by molecular exclusion chromatography.

Expression and Purification of Human Interferon-α5 in *Solanum tuberosum*:

Construction of the expression vector and acquisition of transgenic plants.

The cDNA which codes for interferon-α5 is cloned in an *Agrobacterium tumefaciens* expression vector. This vector contains the potato promoter (the most abundant protein in the *Solanum tuberosum* tubercle), as well as a sequence which codes for a series of histidine residues (1 kDa) and which are translated in phase with the cloned cDNA to yield a merged protein which contains a 1 kDa histidine tail at its terminal amine end followed by interferon-α5, with a site between the two which can be cut by thrombin.

Once the expression vector has heen obtained, competent bacteria of the GV2260 strain of *Agrobacterium tumefaciens* are prepared. The competent bacteria are transformed using the previously obtained vector. The transformed bacteria are selected by growth in LB medium with kanamycin, as the vector contains a gene which is resistant to that antibiotic.

Subsequently a coculture of the transformed bacteria with the plant material (*Solanum tubersosum* leaves cultivated in vitro) is performed and the plant cells resistant to kanamycin are selected. These cells are regenerated until transgenic plants are obtained.

Acquisition and Purification of Interferon-α5:

Total protein extraction is performed from tubercles of the transgenic plants which express the interferon-α5.

The purification of His-interferon-α5 merged protein is carried out by chromatography of the protein extract obtained on a 2 ml nickel column. The protein is eluted by washing the column with 1 M imidazole. The pure protein is processed with thrombin and the interferon-α5 is subsequently repurified using molecular exclusion chromatography.

IFNα Subtypes in Normal Liver Tissue and PBMC in Healthy Individuals

After extraction of the total RNA of the normal liver tissue samples the mRNA of the IFNα was amplified using universal primers for all the IFNα subtypes. The PCR amplification products were then cloned and sequenced. 41 clones from 4 different normal livers were analysed and we observed that the IFNα sequence in the 41 clones was the same and corresponded to the IFNα5 subtype (Table 1). These results show that IFNα5 is the only IFNα subtype expressed in normal liver. The partial cDNA sequence of the IFNα5 obtained from all the clones was shown to be SEQ ID NO: 1.

To compare the profile of the IFN subtypes expressed in the liver with that expressed in PBMC the total RNA of the PBMC from 5 healthy controls was extracted and the IFNα mRNA was amplified with the universal primers for all the IFNα subtypes. Of the 43 clones analysed, 15 corresponded to the IFNα5 subtype, 14 to the IFNα1/13, 6 to the IFNα21 and 8 clones to other IFNα subtypes (Table 1). These results indicate that the IFNα subtype profile expressed in PBMC differs from that expressed in normal liver.

IFNα Subtypes in Liver Tissue and PBMC from Patients with Chronic Hepatitis C

The above results show that the normal liver expresses IFNα5, while PBMC express a variety of IFNα subtypes. In the liver parenchyma of patients with chronic hepatitis C there is mononuclear cell infiltrate, an important source of IFNα. This suggests that the profile of IFNα subtypes expressed by the liver in patients with chronic hepatitis C might differ from the profile found in normal liver. To investigate the expression of IFNα subtypes in chronic hepatitis C we extracted the total RNA from liver samples from 3 different patients and 2 PBMC samples. After amplifying the IFNα mRNA with universal primers for all subtypes, we cloned and sequenced 24 clones of liver tissue and 18 clones of PBMC. As shown in Table 1, the PBMC from patients with chronic hepatitis C expressed IFNα21, IFNα5 and IFNα7 (5, 12, and 1 clones respectively). In the liver tissue from these patients we found subtypes IFNα21, IFNα17 and IFNα1/13 (8, 1 and 2 clones respectively) in addition to the IFNα5 subtype (Table 1).

These data suggest that the production of IFNα by the mononuclear cell infiltrate can cause a change in the profile of IFNα subtypes expressed in the liver tissue of patients with chronic hepatitis C.

Levels of Expression of IFNα mRNA in PBMC and the Liver of Patients with Chronic Hepatitis C and Controls Total RNA was extracted from PBMC and liver samples from patients with chronic hepatitis C (n=25 and 16, respec tively), PBMC samples from healthy controls (n=20) and normal liver tissue samples obtained by laparotomy (n=12). The mRNA levels of IFNα were determined using the semiquantitative reverse transcription-polymerase chain reaction (RT-PCR) technique using universal primers to amplify all the IFNα subtypes. The values are expressed as the ratio of IFNα mRNA to β-actin mRNA.

We found that the levels of expression of IFNα in the PMBC of patients with chronic hepatitis C were significantly increased in comparison with those found in healthy controls (3.2±0.48 against 1.14±0.26; p=0.001) (FIG. 1A). This result was expected in a viral infection such as hepatitis C in which the PBMC are infected (14). On the other hand the levels of expression of IFNα mRNA were significantly reduced in the liver tissue from patients with chronic hepatitis C in comparison with that expressed in normal liver (0.12±0.03 against 0.43±0.12; p=0.003) (FIG. 1B).

As observed previously, IFNα5 is the only IFNα subtype detected in normal liver, while a mixture of subtypes is observed in the liver tissue of patients with chronic hepatitis C. Our findings indicate that in infection by HCV there is a marked reduction in the expression of the IFNα subtype normally expressed in liver tissue. Interestingly, IFNα mRNA levels in the livers of patients with chronic hepatitis C show a direct correlation with the Knodell index (r=0.54; p<0.05). This finding, together with the observation that the IFNα subtypes detected in the livers of patients with chronic hepatitis C are those observed in PBMC suggests that most of the IFNα mRNA found in the liver in hepatitis C comes from the inflammatory infiltrate. It appears possible that the reduction in the expression of liver IFNα (IFNα5) may play a part in making the HCV infection chronic. As a result, these observations may have therapeutic implications if we also bear in mind the marked antiviral and antiproliferative activity of the IFNα5 described by other authors (9).

Levels of Expression of IFN mRNA in the PBMC and Liver of Patients with Chronic Hepatitis C and Controls IFNβ, the second majority form of type 1 interferon, is a glycoprotein produced by a single gene. In viral infections transcription of the IFNα and IFNβ genes is activated or repressed by various mechanisms (15). To analyse the expression of IFNβ in chronic hepatitis C we determined IFNβ mRNA levels in the same samples of liver tissue and PBMC previously used to determine the expression of IFNα.

Figure 2B:
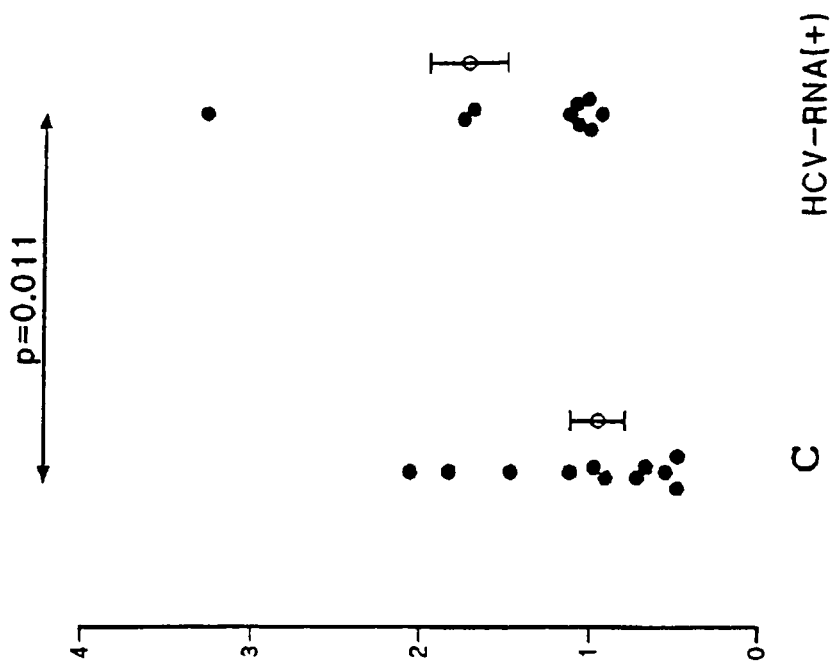
FIGS. 2 A–B: Expression of beta interferon/β-actin RNAm (ordinate) in peripheral blood mononuclear cells (A) and in the liver (B) of healthy controls (C) and patients with chronic hepatitis C (HCV-RNA+) (abscissa).
Figure 2A:
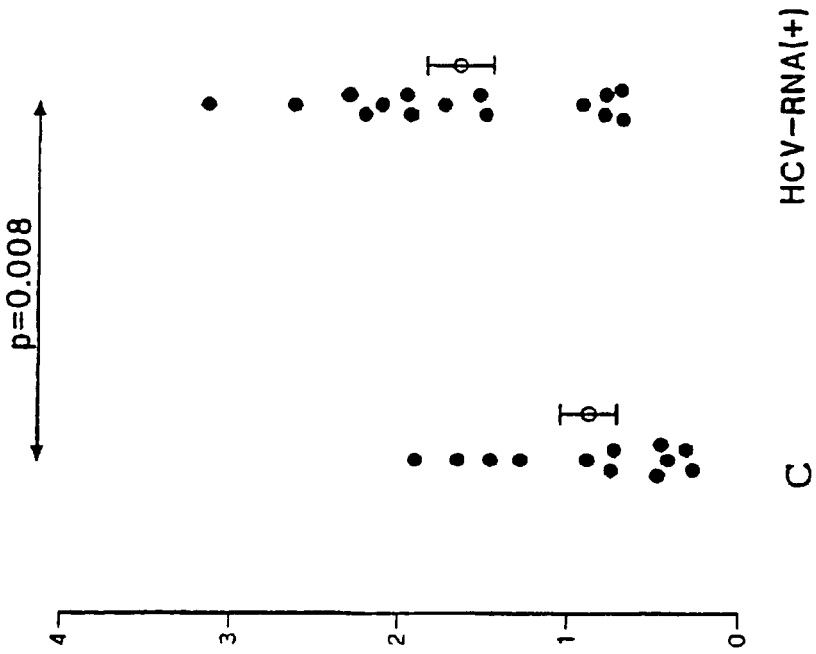

As shown in FIG. 2, we observed that IFNβ mRNA levels (expressed as a ratio against β-actin) were significantly higher in both PBMC and the liver in patients with chronic hepatitis C in comparison with the PBMC findings in healthy controls and normal livers (1.66±0.2 against 0.88±0.16; p=0.008 in PBMC and 1.37±0.23 against 0.97±0.16; p=0.011 in liver). These results show that while HCV causes IFNα to be repressed in the liver, the expression of IFNβ is increased in both the liver and PBMC. This indicates that VHC modulates the different type I IFN genes in the liver in a different way, and blocks the production of IFNα to permit the overexpression of IFNβ.

Relationship Between the Expression of IFNα and IFNβ Genes with Viral Load, Genotype and Liver Damage in Chronic Hepatitis C In order to determine whether the expression of the IFNα or IFNβ genes can be related to viral load or genotype we quantified the C virus RNA in the serum of all patients using the competitive PCR technique and determined the VHC genotype using a hybridization method with specific test materials. We found no correlation between the expression of the IFNα or IFNβ genes (in the liver or PBMC) and C virus RNA levels in serum or the viral genotype. Analysing the relationship between the expression of the type I IFN genes and the severity of liver damage in patients with chronic hepatitis C we found that IFNβ mRNA levels in the liver correlated directly with serum aspartate aminotransferase values (r=0.64, p=0.008) and the Knodell index (r=0.66, p=0.006). Likewise the IFNα mRNA values in the liver showed a direct positive correlation with the Knodell index as mentioned previously.

TABLE 1

IFNα subtypes in controls and patients with chronic hepatitis C.

|  | Liver | PBMC |
|---|---|---|
| Control 1 | 9 IFNA5 clones | |
| Control 2 | 9 IFNA5 clones | |
| Control 3 | 11 IFNA5 clones | |
| Control 4 | 12 IFNA5 clones | |
| Control 5 | | 3 IFNA5 clones |
| | | 4 IFNA21 clones |
| | | 2 IFNA1 clones |
| Control 6 | | 8 IFNA5 clones |
| Control 7 | | 10 IFNA1/13 clones |
| | | 1 IFNA8 clone |
| Control 8 | | 3 IFNA5 clones |
| | | 2 IFNA21 clones |
| | | 2 IFNA1/13 clones |
| | | 1 IFNA22 clones |
| Control 9 | | 2 IFNA10 clones |
| | | 1 IFNA5 clone |
| | | 1 IFNA2 clone |
| | | 1 IFNA7 clone |
| | | 1 IFNA8 clone |
| | | 1 IFNA4 clone |
| RNA-VHC (+) 1 | 6 IFNA5 clones | 7 IFNA5 clones |
| | 2 IFNA21 clones | 1 IFNA21 clone |
| | 1 IFNA17 clone | 1 IFNA7 clone |
| RNA-VHC (+) 2 | 2 IFNA5 clones | 5 IFNA5 clones |
| | 4 IFNA21 clones | 4 IFNA21 clones |
| RNA-VHC (+) 3 | 5 IFNA5 clones | |
| | 2 IFNA21 clones | |
| | 2 IFNA1 clones | |

The invention claimed is:

1. A method of screening a patient suspected of having a liver disease of viral hepatitis C origin, said method comprising assaying liver cells of the patient for reduced levels of IFN-alpha 5.

2. The method according to claim 1 further comprising treating said patient by administering to the patient an amount of IFN-alpha 5 that is effective to raise the level of IFN-alpha 5 in the patient.

3. A method according to claim 2, wherein the liver disease is chronic hepatitis C.

4. A method according to claim 2, wherein the patient has a liver disease that is cirrhosis of viral origin.

5. A method according to claim 2, comprising administering to the patient a recombinant protein comprising said IFN-alpha 5.

6. A method according to claim 5, wherein said recombinant protein is prepared by cloning an expression vector in a procaryotic host organism.

7. A method according to claim 5, wherein said recombinant protein is prepared by cloning an expression vector in *E. coli*.

8. A method according to claim 5, wherein said recombinant protein is prepared by cloning an expression vector in a eukaryotic host organism.

9. A method according to claim 8, wherein the eukaryotic host organism is *Solanum tuberosum*.

* * * * *